(12) United States Patent
Vokrot et al.

(10) Patent No.: US 10,835,336 B2
(45) Date of Patent: *Nov. 17, 2020

(54) HAPTIC FEEDBACK CONTROLS FOR A ROBOTIC SURGICAL SYSTEM INTERFACE

(71) Applicant: Covidien LP, Mansfield, MA (US)

(72) Inventors: Peter Vokrot, Malden, MA (US); William Peine, Ashland, MA (US); Matthew Blanco, Boston, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/717,235

(22) Filed: Dec. 17, 2019

(65) Prior Publication Data

US 2020/0121407 A1    Apr. 23, 2020

Related U.S. Application Data

(63) Continuation of application No. 15/768,196, filed as application No. PCT/US2016/058970 on Oct. 27, 2016, now Pat. No. 10,517,686.

(Continued)

(51) Int. Cl.
*H04B 3/36* (2006.01)
*A61B 34/00* (2016.01)
(Continued)

(52) U.S. Cl.
CPC .............. *A61B 34/76* (2016.02); *A61B 34/30* (2016.02); *A61B 34/37* (2016.02); *A61B 34/73* (2016.02); *A61B 34/74* (2016.02); *B25J 3/04* (2013.01); *B25J 13/025* (2013.01); *G05G 5/03* (2013.01); *G06F 3/016* (2013.01); *G06F 3/0346* (2013.01); *A61B 34/25* (2016.02); *A61B 90/361* (2016.02);
(Continued)

(58) Field of Classification Search
CPC .................... A61B 34/30; A61B 34/25; A61B 2018/00303; A61B 2034/731; A61B 34/76; A61B 19/2203; A61B 18/082
See application file for complete search history.

(56) References Cited

U.S. PATENT DOCUMENTS 6,184,868 B1   2/2001   Shahoian et al.
6,232,891 B1   5/2001   Rosenberg
(Continued)

FOREIGN PATENT DOCUMENTS

WO   2014116782 A1   7/2014

OTHER PUBLICATIONS

International Search Report dated Feb. 7, 2017 in PCT/US2016/058970.

(Continued)

*Primary Examiner* — Toan N Pham

(57) ABSTRACT

A gimbal for a robotic surgical system includes a support link, an input link, and a vibration assembly. The input link extends from the support link and the vibration assembly is mounted to the support link. The vibration assembly includes a central support, an end cap, and a voice coil. The end cap is moveable relative to the central support. The voice coil has an inner member that is fixed to the central support and an outer member that is fixed to the end cap. The voice coil is configured to vibrate the gimbal in response to a voltage being applied to one of the inner or outer members.

15 Claims, 7 Drawing Sheets

Related U.S. Application Data

(60) Provisional application No. 62/248,516, filed on Oct. 30, 2015.

(51) Int. Cl.
| | |
|---|---|
| *A61B 34/37* | (2016.01) |
| *G05G 5/03* | (2008.04) |
| *B25J 13/02* | (2006.01) |
| *G06F 3/01* | (2006.01) |
| *B25J 3/04* | (2006.01) |
| *G06F 3/0346* | (2013.01) |
| *A61B 34/30* | (2016.01) |
| *A61B 17/00* | (2006.01) |
| *A61B 18/00* | (2006.01) |
| *A61B 90/00* | (2016.01) |
| *G05G 9/047* | (2006.01) |

(52) U.S. Cl.
CPC ..... *A61B 90/37* (2016.02); *A61B 2017/00115* (2013.01); *A61B 2017/00221* (2013.01); *A61B 2018/00303* (2013.01); *A61B 2018/00595* (2013.01); *A61B 2034/731* (2016.02); *A61B 2090/064* (2016.02); *A61B 2090/367* (2016.02); *A61B 2090/376* (2016.02); *A61B 2090/378* (2016.02); *G05B 2219/40132* (2013.01); *G05G 2009/04718* (2013.01); *G05G 2009/04766* (2013.01)

(56) References Cited

U.S. PATENT DOCUMENTS

| | | | |
|---|---|---|---|
| 6,377,011 | B1 | 4/2002 | Ben-Ur |
| 8,663,122 | B2 | 3/2014 | Schecter |
| 8,828,023 | B2 | 9/2014 | Neff et al. |
| 10,517,686 | B2 * | 12/2019 | Vokrot .................. G06F 3/016 |
| 2001/0000663 | A1 | 5/2001 | Shahoian et al. |
| 2011/0115754 | A1 | 5/2011 | Cruz-Hernandez |
| 2012/0116364 | A1 | 5/2012 | Houser et al. |
| 2014/0188128 | A1 | 7/2014 | Weber |

OTHER PUBLICATIONS

Extended European Search Report dated May 20, 2019 corresponding to counterpart Patent Application EP 16860739.8.

* cited by examiner

HAPTIC FEEDBACK CONTROLS FOR A ROBOTIC SURGICAL SYSTEM INTERFACE

CROSS-REFERENCE TO RELATED APPLICATIONS

This application is a Continuation application which claims the benefit of and priority to U.S. patent application Ser. No. 15/768,196, filed Apr. 13, 2018, which is a U.S. National Stage Application filed under 35 U.S.C. § 371(a) of International Patent Application Serial No. PCT/US2016/058970, filed Oct. 27, 2016, which claims the benefit of and priority to U.S. Provisional Patent Application Ser. No. 62/248,516, filed Oct. 30, 2015, the entire disclosure of each of which is incorporated by reference herein.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes a handle or gimbal that is moveable by the surgeon to control the robotic system.

There is a need for improved feedback systems for providing haptic feedback to a surgeon interfacing with the user interface during a surgical procedure.

SUMMARY

In an aspect of the present disclosure, a gimbal for a surgical robotic system includes a support link, an input link extending from the support link, and a vibration assembly mounted to the support link. The vibration assembly includes a central support, an end cap, and a voice coil. The end cap is movable relative to the central support. The voice coil has an inner member that is fixed to the central support and an outer member that is fixed to the end cap. The voice coil is configured to vibrate the gimbal in response to a voltage being applied to one of the inner or outer members.

In aspects, the central support includes a central portion and a flange that extends radially from the central portion. The vibration assembly may include an inner plate that is positioned about the central portion of the central support with the flange of the central portion positioned between the end cap and the inner plate. The inner plate and the end cap may be made from a non-magnetic metal or a plastic. The inner plate may be fixed relative to the end cap.

In some aspects, the vibration assembly includes a first dampening ring that is positioned between the end cap and the flange of the central portion. The first dampening ring may be positioned about the outer member of the voice coil and may be bonded to the end cap and the flange. The vibration assembly may include a second dampening ring that is positioned between the flange of the central portion and the inner plate. The second dampening ring may be positioned about the inner member of the voice coil and may be bonded to the flange and the inner plate. The first and second dampening rings may be made from an elastomeric material.

In certain aspects, the inner member of the voice coil includes a conductive coil and the outer member of the voice coil is a magnet. The outer member may move in a first direction relative to the inner member when a first voltage is applied to the conductive coil and may move in a second direction opposite the first direction when a second voltage is applied to the conductive coil. The first voltage may be a positive voltage and the second voltage may be a negative voltage.

In another aspect of the present disclosure, a robotic surgical system includes a robotic system, a processing unit, and a user interface having a gimbal. The robotic system includes a linkage that has a tool disposed at one end. The processing unit is in communication with the robotic system to manipulate the tool. The user interface is in communication with the processing unit and is configured to provide a control signal to the processing unit for manipulating the tool. The gimbal includes a support link, an input link that extends from the support link, and a vibration assembly that is mounted to the support link. The vibration assembly includes a central support, an end cap that is movable relative to the central support, and a voice coil. The voice coil includes an inner member that is fixed to the central support and an outer member that is fixed to the end cap. The processing unit is configured to provide a feedback signal indicative of a condition of the robotic surgical system. The voice coil is configured to vibrate the gimbal in response to the feedback signal.

In aspects, the voice coil assembly includes a vibration control that is configured to apply a voltage to one of the inner or outer members in response to the feedback signal. The robotic surgical system may include an intensity switch that is configured to adjust the intensity of the vibration of the gimbal in response to the feedback signal. The feedback signal may be indicative of one or more conditions of the robotic surgical system including, but not limited to, the tool reaching an end of a range, the gimbal being clutched, a need to clutch the gimbal, the gimbal being switched to a camera control state, a state change of the tool, a presence of a message on a display of the user interface, the tool being changed, a collision of the tool with another tool, the tool approaching a target, the tool contacting a structure, vibration of the tool, or a measurement of a grasping force of the tool.

In another aspect of the present disclosure, a method of controlling a robotic surgical system with haptic feedback includes manipulating an input device coupled to a gimbal of a user interface of the robotic surgical system to manipulate a tool of a robot system of the robotic surgical system, receiving a feedback signal from a processing unit of the robotic surgical system with a vibration controller, and oscillating a vibration assembly in response to the feedback signal to vibrate the gimbal. The vibration controller is in communication with the vibration assembly that is mounted to the gimbal of the user interface. The vibration of the gimbal provides an indication of a condition of the robotic surgical system.

In aspects, the method includes detecting vibration of the gimbal and adjusting the oscillation of the vibration assembly in response to the detected vibration of the gimbal. Oscillating the vibration assembly in response to the feedback signal may include vibrating the gimbal in a first manner in response to a first condition of the robotic surgical system and vibrating the gimbal in a second manner in response to a second condition of the robotic surgical system. The second manner is different from the first manner. Vibrating the gimbal in the second manner that is different from the first manner may include varying the frequency, amplitude, waveform, or duration of the vibration.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
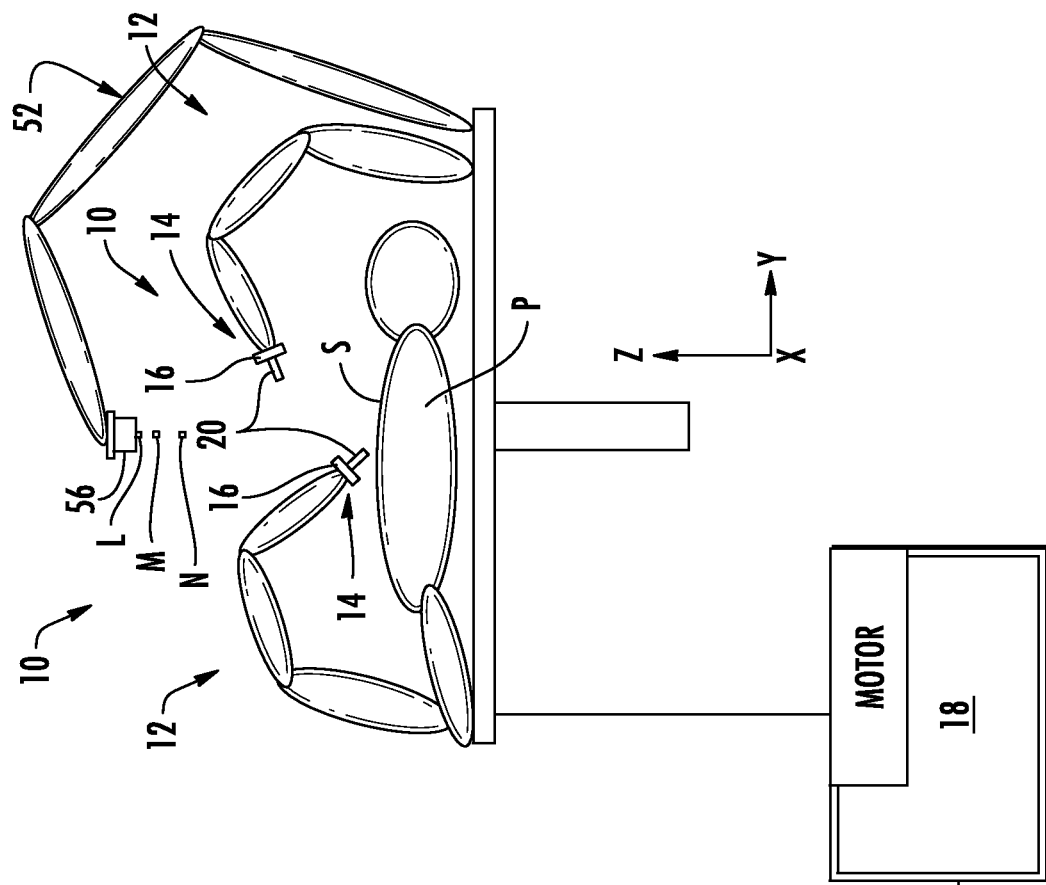
FIG. 1 is a schematic illustration of a user interface and a robotic system in accordance with the present disclosure.
Figure 1:
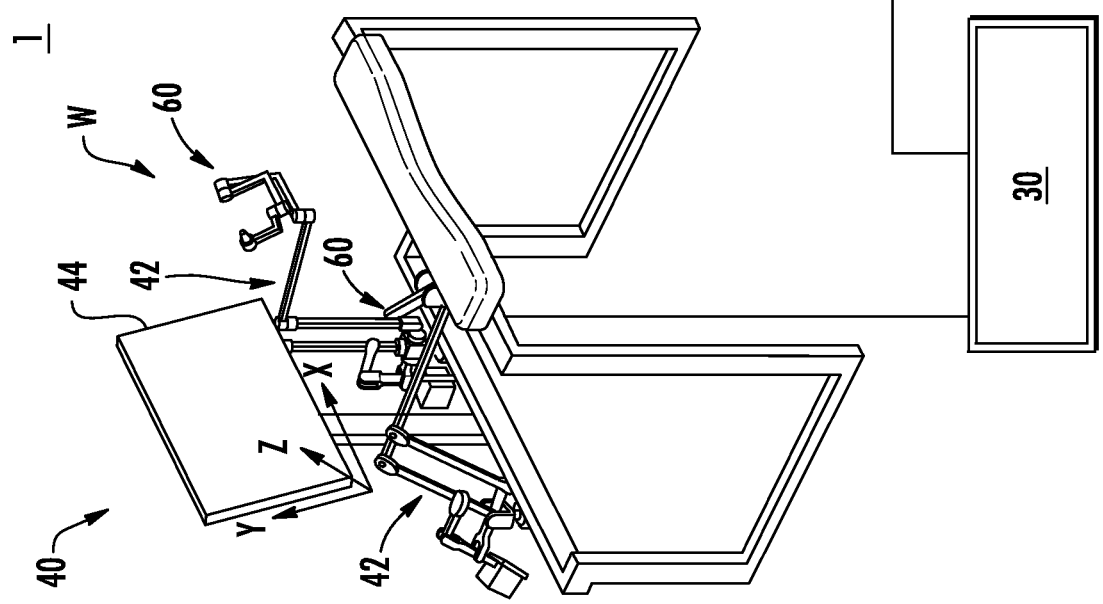

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

The present disclosure relates generally to vibration mechanisms for providing feedback during a surgical procedure to a clinician operating a robotic surgical system. The vibration mechanisms are mounted to a gimbal of a user interface of a robotic surgical system. As a clinician interfaces with the user interface, the vibration mechanisms provide haptic or audible feedback to the clinician. As shown throughout this disclosure, the vibration mechanism is shown as a vibration voice coil; however, it is contemplated that other vibration mechanisms (e.g., piezo motors) may be used.

Referring to FIG. 1, a robotic surgical system 1 in accordance with the present disclosure is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of links each having an end 14 that supports an end effector or tool 20 which is configured to act on tissue. In addition, the ends 14 of the linkages 12 may include an imaging device 16 (e.g., an endoscope or the like) for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the linkages 12 and/or include data captured by imaging devices that are positioned about the surgical theater (e.g., an imaging device positioned within the surgical site "S", an imaging device positioned adjacent the patient "P", imaging device 56 positioned at a distal end of an imaging link 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input links 42 that each support a gimbal 60. The gimbals 60 allow a clinician to manipulate the robotic system 10 (e.g., move the linkages 12, move the ends 14 of the linkages 12, and/or manipulate the tools 20). Each of the input handles 42 and/or gimbals 60 are in communication with the processing unit 30 to transmit control signals thereto and to receive feedback signals therefrom.

For a detailed discussion of the construction and operation of a robotic surgical system 1, reference may be made to U.S. Pat. No. 8,828,023 the entire contents of which are incorporated herein by reference.

Figure 2:
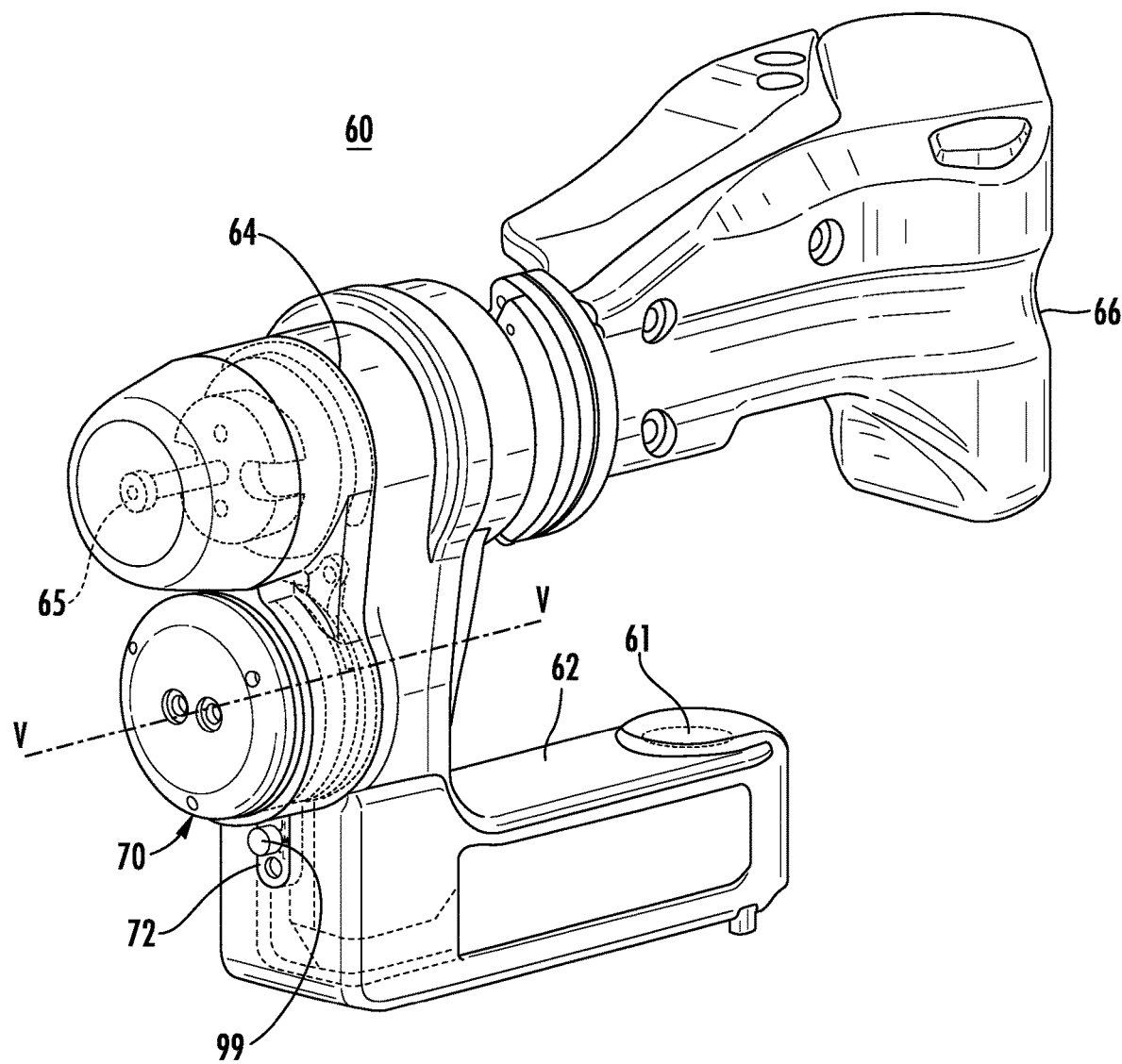
FIG. 2 is an enlarged perspective view of a gimbal of the user interface of FIG. 1.

With additional reference to FIG. 2, each of the gimbals 60 includes a lower support link 62 and a vertical support link 64. One end of the lower support link 60 defines an opening 61 that is rotatably supported on the end of an input link 42 of the user interface 40 and the other end of the lower support link 60 supports the vertical support link 64 extending perpendicular (e.g., vertically) from the lower support link 62. The vertical support link 64 extends parallel to an axis of the opening 61. The vertical support link 64 supports an input shaft 65 that extends perpendicular to the vertical support link 64 and parallel to the lower support link 62.

An input device 66 is supported on the input shaft 65 to allow a clinician to manipulate (e.g., clamp, grasp, fire, open, close, rotate, thrust, slice, etc.) the tools 20 (FIG. 1) supported at the ends 14 of the linkages 12. The input device 66 is rotatable about the input shaft 65 and may be slidable along the input shaft 65.

A vibration voice coil assembly 70 is mounted to the vertical support link 64 between lower support link 62 and the input shaft 65 by a mounting plate 72. Alternatively, the vibration voice coil assembly 70 may be mounted in the vertical support link 64. The vibration voice coil assembly 70 defines a vibration axis V-V that is positioned approximately halfway between the lower support link 62 and the input shaft 65. The vibration axis V-V is or may be parallel to the input shaft 65 and the lower support link 62. As detailed below, the vibration voice coil assembly 70 is activated to provide vibratory or haptic feedback to a clinician engaged with or holding the input device 66. In addition, the vibration voice coil assembly 70 may provide auditory feedback to a clinician engaged with or adjacent the input device 66.

Figure 3:
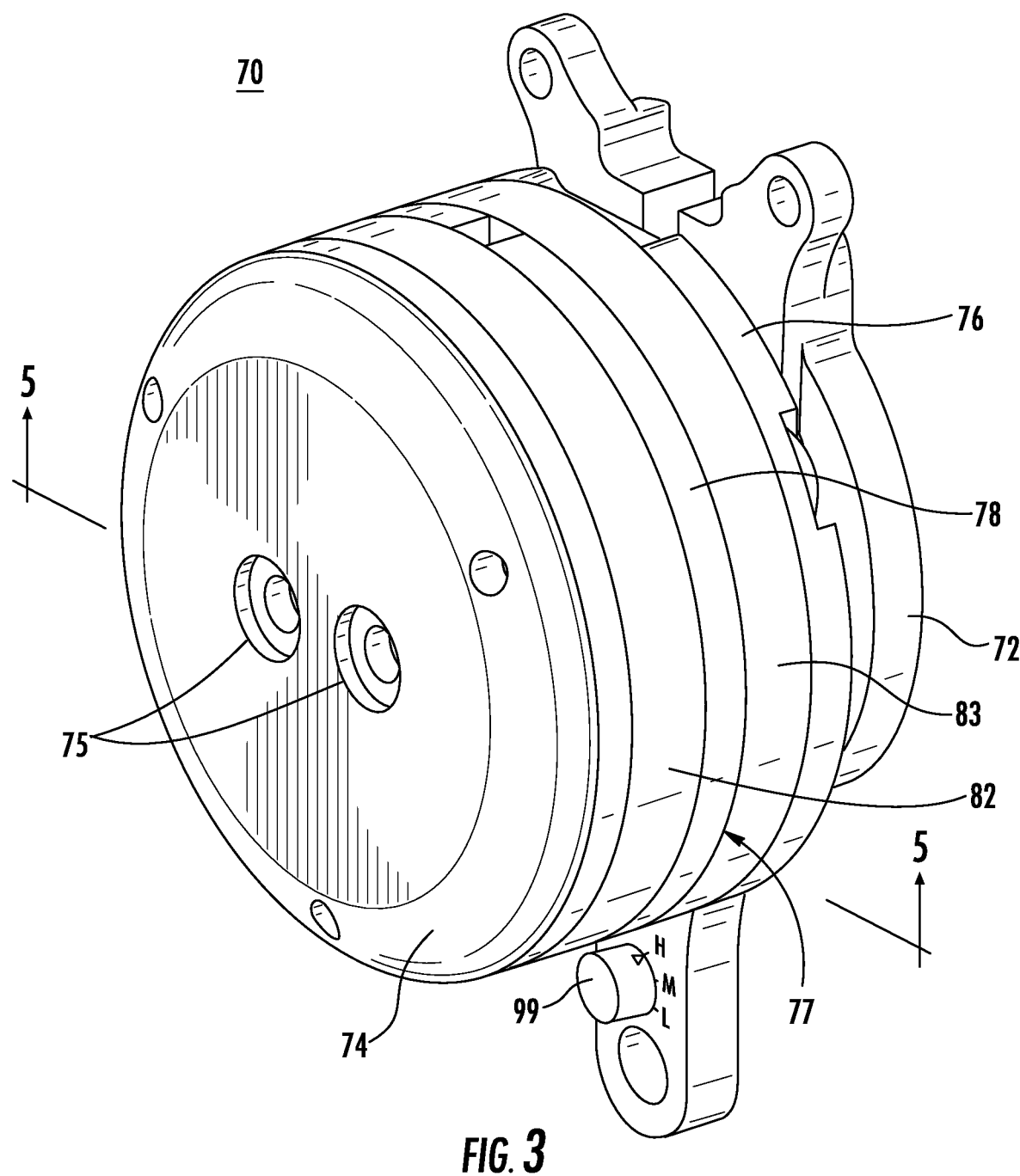
FIG. 3 is a front perspective view of a vibration voice coil of the gimbal of FIG. 2.
Figure 4:
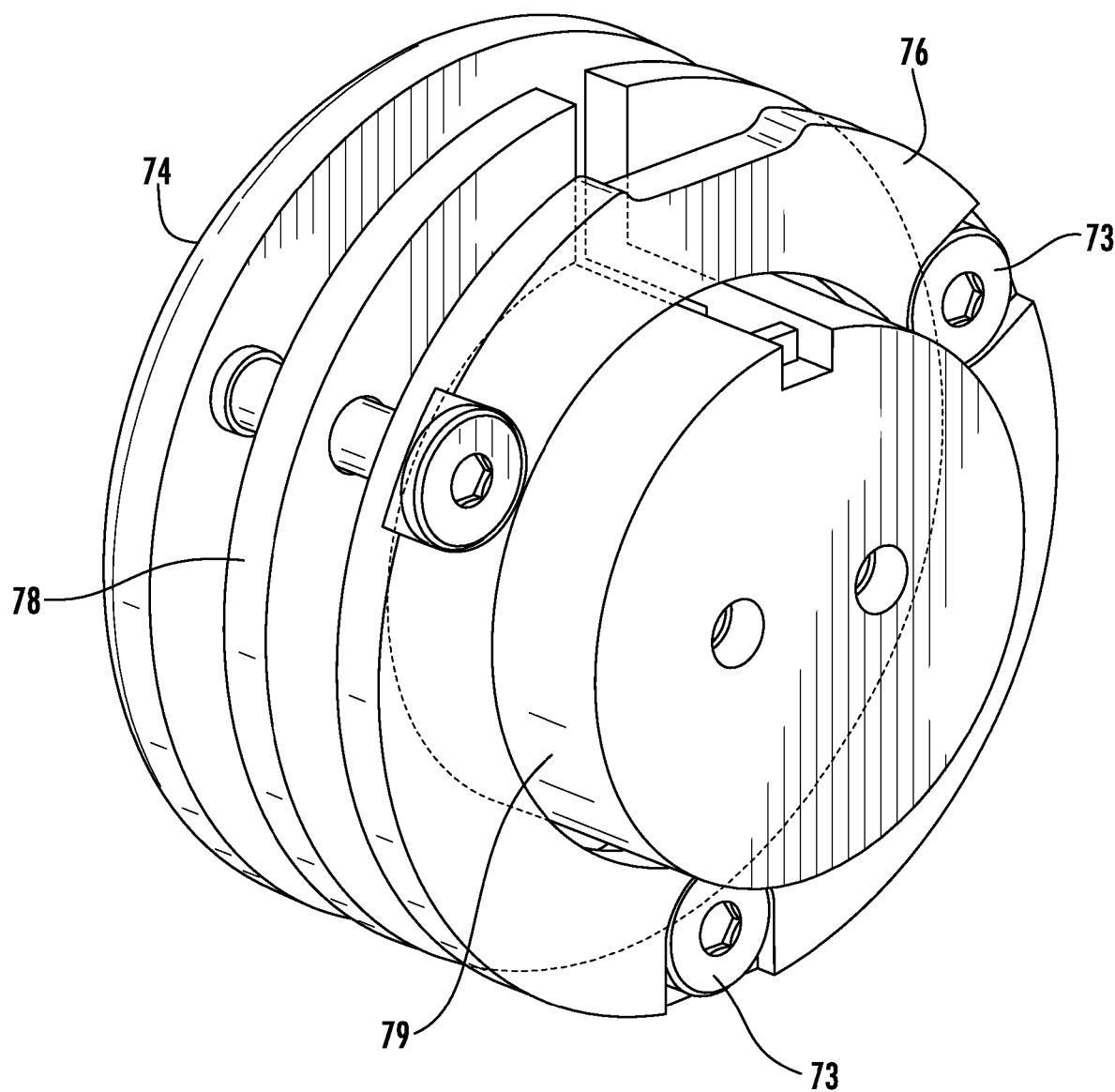
FIG. 4 is a rear perspective view of the vibration voice coil of FIG. 3 with the mounting plate removed.
Figure 5:
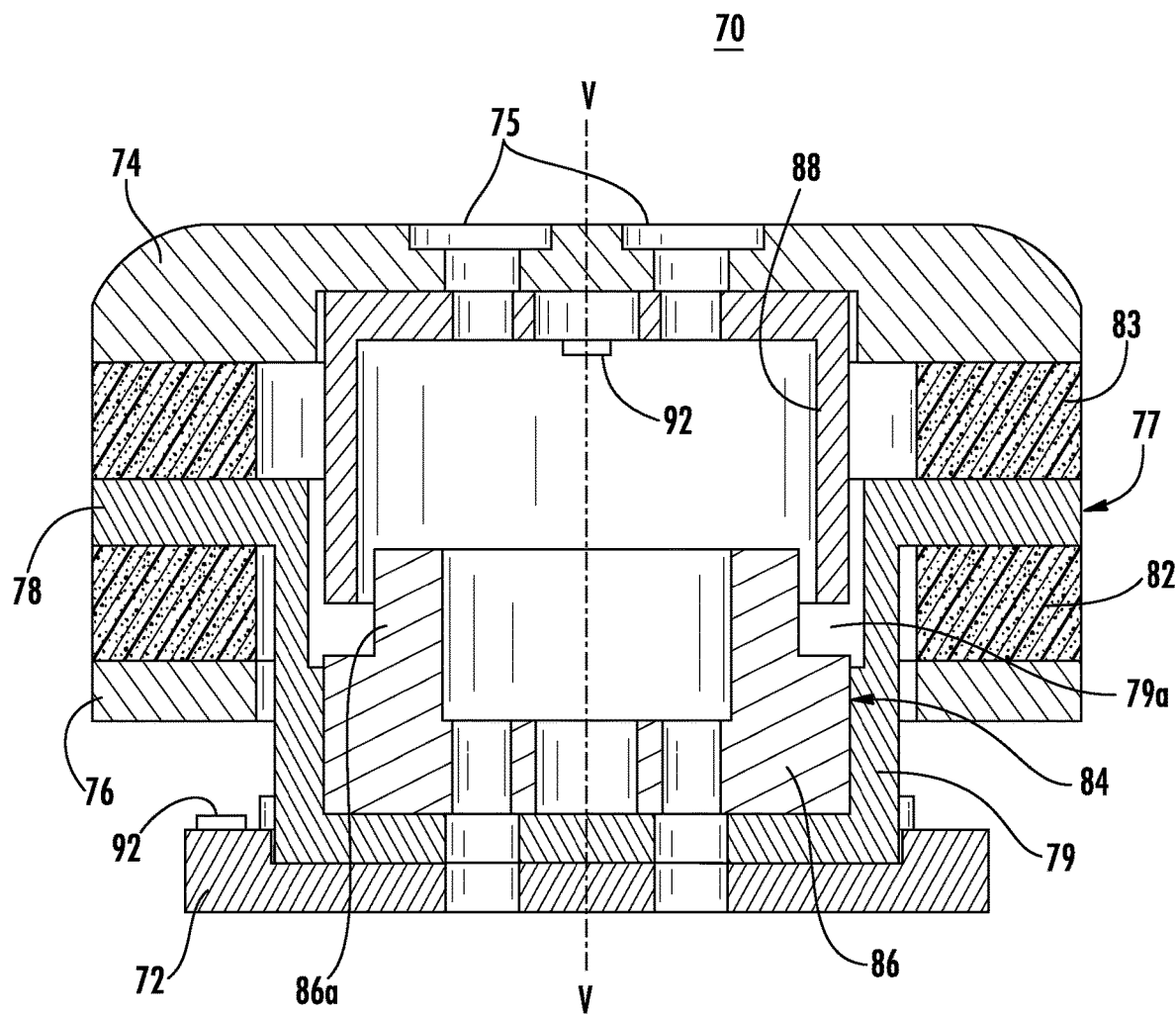
FIG. 5 is a cross-sectional view taken along the section line 5-5 of FIG. 3.

With reference to FIGS. 3-5, the vibration voice coil assembly 70 includes an end cap 74, an inner plate 76, a central support 77, dampening rings 82, 83, and a voice coil 84. With particular reference to FIG. 5, the central support 77 includes a flange 78 positioned between the end cap 74 and the inner plate 76 and a central portion 79 extending from the flange 78, through the inner plate 76, and fixed to the mounting plate 72. The central portion 79 is substantially cylindrical and defines a cavity 79a that receives the voice coil 84 therein. The voice coil 84 includes an inner member 86 fixed within the cavity 79a of the central portion 79 adjacent the mounting plate 72, an outer member 88 fixed to the end cap 74, and disposed atop or adjacent the inner member 86 of the voice coil 84.

The end cap 74 is positioned on a side of the flange 78 of the central support 77 away from the mounting plate 72. The inner plate 76 is positioned about the cylindrical central portion 79 of the central support 77 between the flange 78 and the mounting plate 72. The end cap 74 is fixed to the outer member 88 of the voice coil 84. The dampening ring 82 is positioned between the end cap 74 and the flange 78 of the central support 77. The inner plate 76 is positioned between the flange 78 of the central support 77 and the mounting plate 72. The dampening ring 83 is positioned between the inner plate 76 and the flange 78 of the central support 77. The inner plate 76 is fixed to the end cap 74 by fasteners 73 (FIG. 4). The fasteners 73 slidably pass through the flange 78 such that the end cap 74 and the inner plate 76 float relative to the flange 78 along the vibration axis V-V. The end cap 74 and the outer member 88 of the voice coil 84 include openings 75 to permit air to pass as the end cap 74 moves relative to the central support 77.

The voice coil 84 is a magnetic voice coil and operates in response to changes in a magnetic field such that changes in the magnetic field expand and contract the inner and outer members 86, 88 of the voice coil 84 relative to one another. A portion of the outer member 88 of the voice coil 84 is positioned between the cylindrical central portion 79 of the central support 77 and a stem portion 86a of the inner member 86 of the voice coil 84. The outer member 88 of the voice coil 84 may be a magnetic housing and the inner member 86 may include a conductive coil such that as a voltage (e.g., a positive voltage) is applied to the inner member 86 to generate a first magnetic field, the outer member 88 is moved in a first direction (e.g., away from the inner member 86) and when a second voltage (e.g., a negative voltage) is applied to the inner member 86 to generate a second magnetic field, the outer member 88 is moved in a second direction (e.g., towards the inner member 86) opposite the first direction.

As shown, the voice coil 84 is a cylindrical linear voice coil; however, it is contemplated that the voice coil 84 may have different shapes (e.g., rectangular, triangular, or octagonal) or be a rotary voice coil.

The end cap 74 and the inner plate 76 are constructed from a non-magnetic material such that the end cap 74 and the inner plate 76 are substantially rigid without interfering with operation of the voice coil 84. In addition, the end cap 74 and the inner plate 76 are constructed from a material having a sufficiently high mass such that oscillation of the end cap 74 and the inner plate 76 produces a vibration of the input device 66. Similarly, the central support 77 is constructed from a non-magnetic material that is substantially rigid without interfering with the operation of the voice coil 84. Non-limiting examples of materials for the end cap 74, inner plate 76, and central support 77 are non-magnetic metals such as aluminum and aluminum alloys, and plastics such as acetal plastics.

The dampening rings 82, 83 of the voice coil assembly 70 are constructed of an elastomeric material to act as a spring and/or damper in response to movement of the end cap 74 and the inner plate 76. The dampening rings 82, 83 are sized to maintain the flange 78 of the central support 77 in a rest or neutral position halfway between the end cap 74 and the inner plate 76 when no voltage is applied to the voice coil 84. The dampening rings 82, 83 may be attached or bonded to the end cap 74, the inner plate 76, and the flange 78 such that the dampening rings 82, 83 may respectively expand and compress from a neutral dimension as the end cap 74 and the inner plate 76 move respectively in the first and second directions relative to the flange 78. It is contemplated that the dampening rings 82, 83 may be constructed of a super-resilient, super-soft polyurethane foam or a PORON® foam; however, other rubbers and foams are also contemplated.

Figure 6:
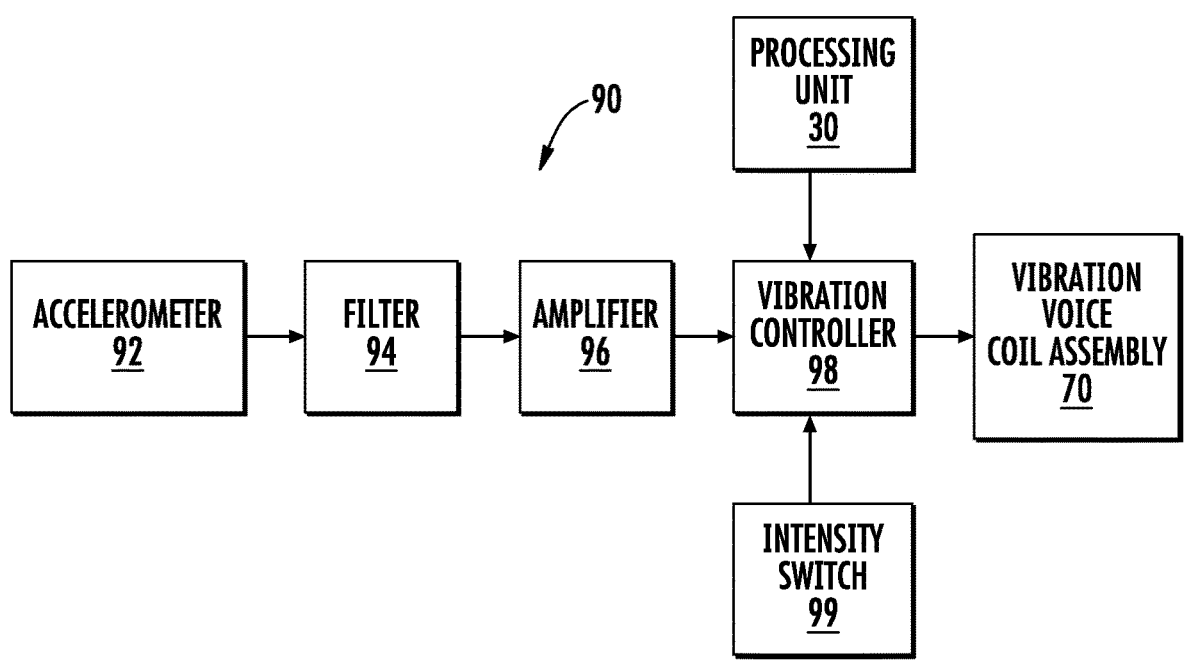
FIG. 6 is a schematic diagram of a control circuit of the vibration voice coil assembly.

Referring to FIG. 6, the vibration voice coil assembly 70 may operate as an open loop system or may include a feedback loop (e.g., control circuit 90) that receives a feedback signal from the processing unit 30 to maintain oscillation of the vibration voice coil assembly 70 in a desired frequency band. The control circuit 90 controls oscillation of the vibration voice coil assembly 70 in response to the feedback signal. The control circuit 90 includes a vibration measuring device (e.g., accelerometer 92), a filter 94, an amplifier 96, and a vibration controller 98. The accelerometer 92 measures the oscillation and/or the vibration of the gimbal 60 in response to the oscillation of the vibration voice coil assembly 70. Alternatively, the accelerometer 92 may measure the oscillation of the vibration voice coil assembly 70. The accelerometer 92 transmits a vibration signal to the filter 94 which eliminates noise from the vibration signal. Additionally or alternatively, the filter 94 may process and shape the waveform of the vibration signal to optimize vibrations for tactile feedback sensitivity. Such processing and shaping may be customizable for each clinician and/or tool 20 (FIG. 1) attached to a respective link 12. The filter 94 transmits the filtered vibration signal to the amplifier which amplifies the filtered vibration signal. The amplified vibration signal is transmitted from the amplifier 96 to the vibration controller 98. It is contemplated that portions of the control circuit 90 may be integrated within the processing unit 30.

The vibration controller 98 is in communication with the processing unit 30 and transmits a control signal to the vibration voice coil assembly 70 to oscillate the vibration voice coil assembly 70 in response to the feedback signal. The feedback signal is indicative of a condition of the robotic surgical system 1. The condition of the robotic surgical system 1 may include, but is not limited to, the tool 20 reaching an end of range, the gimbal 60 being clutched in or out, the need to clutch a gimbal 60, the gimbal 60 being switched to a camera control state, a state or mode change of the tool 20 (e.g., cauterization mode, staple firing mode), the presence of a message on the display 44, a tool 20 being changed, collision avoidance (e.g., collision of tools 20), a tool 20 approaching a target, a tool 20 contacting a structure, vibration of a tool 20, a measurement of a grasping force of a tool 20. It is contemplated that the condition of the robotic surgical system 1 may include the status of the patient "P" (e.g., vital signs of the patient "P") and/or the status of the clinician (e.g., the robotic surgical system 1 may include a clinician attention monitor (not shown) that provides feedback of the direction of the clinician's gaze).

The vibration controller 98 may uniquely oscillate the vibration voice coil 70 for each condition of the robotic surgical system 1. The vibration controller 98 may vary the frequency, amplitude, waveform, and duration of the oscillation of the vibration voice coil 70 for each condition of the robotic surgical system 1. For example, the vibration controller 98 may oscillate the vibration voice coil 70 for 0.25 seconds when the gimbal 60 must be clutched for continued movement of a tool 20 and may oscillate the vibration voice coil 70 for 1.00 seconds when a tool 20 reaches an end of range. Additionally or alternatively, the vibration controller 98 may oscillate the vibration voice coil 70 for two short pulses when the tool 20 is in a cauterization mode and for three short pulses when the tool 20 is in a staple firing mode. It is contemplated that the vibration controller 98 may be customizable for a clinician.

The vibration controller 98 may be in communication with an intensity switch 99 that allows a clinician to select an intensity of the oscillation of the vibration voice coil 70. As shown, the intensity switch 99 is a rotary switch positioned on the vibration voice coil 70; however, it is contemplated that the intensity switch 99 may be positioned on the gimbal 60 or is accessible through the display 44 of the user interface (e.g., an on screen menu). It is also contemplated that the intensity switch 99 may be a toggle switch, a slide switch, a jumper switch, or a button switch. The intensity switch 99 includes high, medium, and low intensity settings for the vibration voice coil 70.

As detailed above, the vibration voice coil assembly 70 is positioned on the gimbal 60; however, it is contemplated that one or more vibration voice coil assemblies 70 may be positioned on or in an input link 42 (FIG. 1) of the user interface 40 which supports the gimbal 60.

Figure 7:
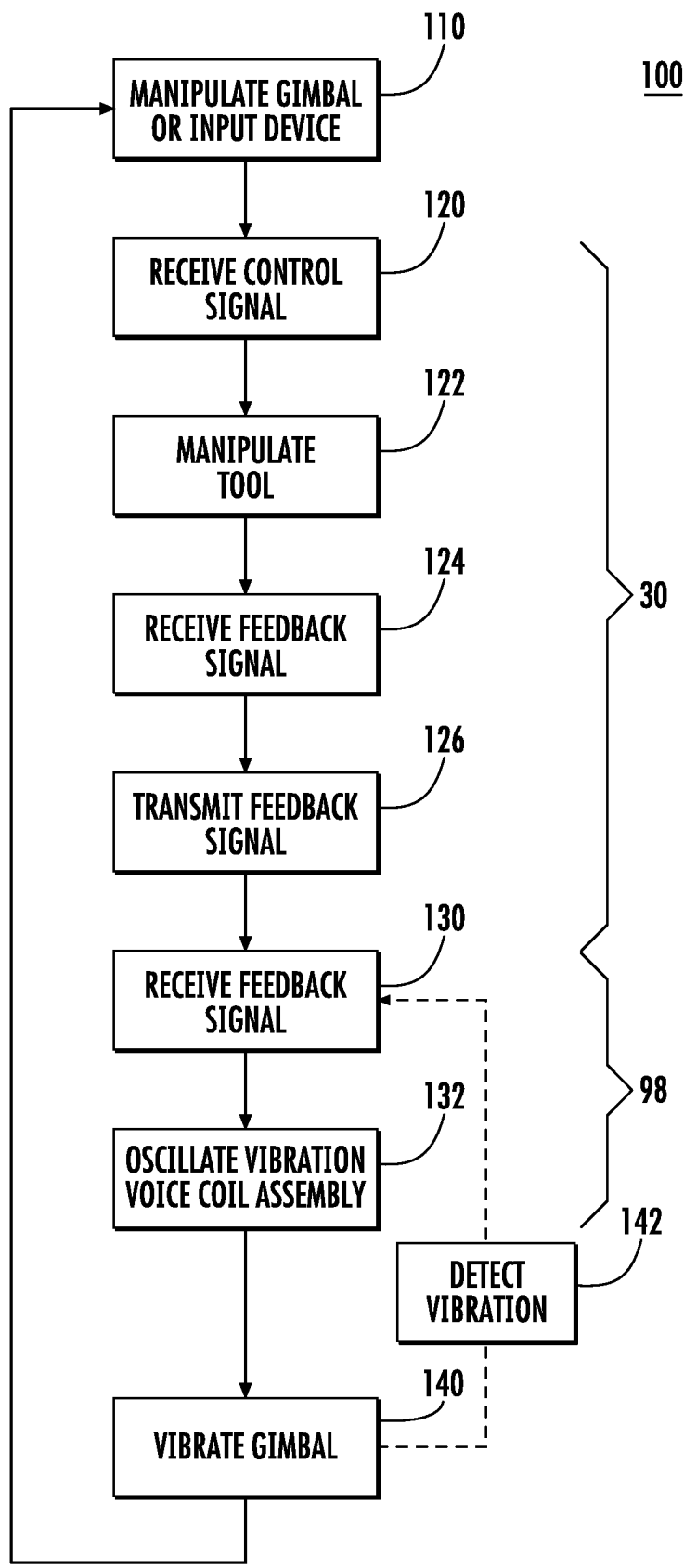
FIG. 7 is a schematic diagram of a method for manipulating a robotic surgical system in accordance with the present disclosure.

With reference to FIG. 7, a method 100 of controlling a tool 20 of a robotic system 10 with haptic feedback is disclosed in accordance with the present disclosure. A clinician engages an input device 66 of a gimbal 60 of a user interface 40 of a robotic surgical system 1 to manipulate (e.g., move or actuate) a tool 20 attached to an end 14 of a linkage 12 (Step 110). The processing unit 30 receives a control signal from the user interface 40 in response to manipulation of the input device 60 (Step 120). In response to the control signal from the user interface 40, the processing unit 30 manipulates the tool 20 (Step 122). The processing unit 30 receives a feedback signal from the robotic system 10 in response to manipulation of the tool 20 and transmits feedback signal to a vibration voice coil assembly 70 mounted to the gimbal 60 (Steps 124, 126).

The vibration controller 98 receives the feedback signal from the processing unit 30 (Step 130). The feedback signal is indicative of a condition of the robotic surgical system 1. In response to the feedback signal, the vibration controller oscillates the vibration voice coil assembly 70 along a vibration axis to induce vibration of the gimbal 60 and the input device 66 (Steps 132, 140). The vibration of the gimbal 60 and the input device 66 provides audible or haptic feedback to the clinician to a condition of the robotic surgical system 1 including a condition of the tool 20. A clinician may manipulate the user interface 40 in response to the haptic feedback (Step 110).

As detailed above, accelerometer 92 may detect vibration of the gimbal 60 or the input device 66 and provide a vibration signal to the vibration controller in response to vibration of the gimbal 60 or the input device 66 (Step 142). The vibration signal may be received by the vibration controller 98 with the feedback signal from the processing unit 30 and be used to adjust the oscillation of the vibration voice coil assembly 70 in response to vibration detected by the accelerometer 92.

The wireless connections detailed herein (e.g., between vibration controller 98 and the processing unit 30) may be via radio frequency, optical, WIFI, Bluetooth® (an open wireless protocol for exchanging data over short distances (using short length radio waves) from fixed and mobile devices, creating personal area networks (PANs)), ZigBee® (a specification for a suite of high level communication protocols using small, low-power digital radios based on the IEEE 802.15.4-2003 standard for wireless personal area networks (WPANs)), etc.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgeon user interface for a surgical robotic system, the surgeon user interface comprising:
   a gimbal, including:
      at least one support link;
      an input link extending from the at least one support link; and
      a vibration assembly mounted to the at least one support link, the vibration assembly including:
         a central support including a central portion and a flange extending radially from the central portion;
         an end cap moveable relative to the central support; and
         a voice coil having an inner member fixed to the central support and an outer member fixed to the end cap, the voice coil configured to vibrate the gimbal in response to a voltage being applied to one of the inner or outer members.

2. The surgeon user interface according to claim 1, wherein the vibration assembly includes an inner plate positioned about the central portion of the central support with the flange of the central portion positioned between the end cap and the inner plate.

3. The surgeon user interface according to claim 2, wherein the inner plate and the end cap of the vibration assembly are made from a non-magnetic metal.

4. The surgeon user interface according to claim 2, wherein the inner plate and the end cap of the vibration assembly are made from a plastic.

5. The surgeon user interface according to claim 2, wherein the inner plate of the vibration assembly is fixed relative to the end cap.

6. The surgeon user interface according to claim 2, wherein the vibration assembly includes a first dampening ring positioned between the end cap and the flange of the central portion.

7. The surgeon user interface according to claim 6, wherein the first dampening ring of the vibration assembly is positioned about the outer member of the voice coil.

8. The surgeon user interface according to claim 6, wherein the first dampening ring of the vibration assembly is bonded to the end cap and to the flange.

9. The surgeon user interface according to claim 6, wherein the vibration assembly includes a second dampening ring positioned between the flange of the central portion and the inner plate.

10. The surgeon user interface according to claim 9, wherein the second dampening ring of the vibration assembly is positioned about the inner member of the voice coil.

11. The surgeon user interface according to claim 9, wherein the second dampening ring of the vibration assembly is bonded to the flange and to the inner plate.

12. The surgeon user interface according to claim 9, wherein the first and second dampening rings of the vibration assembly are made from an elastomeric material.

13. A user interface for a surgical robotic system, the user interface comprising:
a gimbal including:
at least one support link;
an input link extending from the at least one support link; and
a vibration assembly mounted to the at least one support link, the vibration assembly including:
a central support;
an end cap moveable relative to the central support; and
a voice coil having an inner member fixed to the central support and an outer member fixed to the end cap, the voice coil configured to vibrate the gimbal in response to a voltage being applied to one of the inner or outer members, wherein the inner member of the voice coil includes a conductive coil and the outer member of the voice coil is a magnet.

14. The user interface according to claim 13, wherein the outer member of the vibration assembly:
moves in a first direction relative to the inner member thereof when a first voltage is applied to the conductive coil; and
moves in a second direction opposite the first direction when a second voltage is applied to the conductive coil.

15. The user interface according to claim 13, wherein the first voltage is a positive voltage and the second voltage is a negative voltage.

* * * * *